United States Patent
Lee et al.

(10) Patent No.: US 10,434,027 B2
(45) Date of Patent: Oct. 8, 2019

(54) RECOGNITION METHOD OF HUMAN WALKING SPEED INTENTION FROM SURFACE ELECTROMYOGRAM SIGNALS OF PLANTAR FLEXOR AND WALKING SPEED CONTROL METHOD OF A LOWER-LIMB EXOSKELETON ROBOT

(71) Applicant: Korea Institute of Science and Technology, Seoul (KR)

(72) Inventors: Jong Min Lee, Seoul (KR); Hyungmin Kim, Seoul (KR); Seung-Jong Kim, Seoul (KR); Junho Choi, Seoul (KR); Yoha Hwang, Seoul (KR); Sang Hun Chung, Seoul (KR); Yeonghun Kim, Seoul (KR); Junhyuk Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 933 days.

(21) Appl. No.: 15/001,891

(22) Filed: Jan. 20, 2016

(65) Prior Publication Data
US 2017/0056275 A1 Mar. 2, 2017

(30) Foreign Application Priority Data
Aug. 31, 2015 (KR) .................. 10-2015-0123027

(51) Int. Cl.
*A61H 3/00* (2006.01)
*A61B 5/103* (2006.01)
(Continued)

(52) U.S. Cl.
CPC .......... *A61H 3/00* (2013.01); *A61B 5/04888* (2013.01); *A61B 5/1038* (2013.01); *A61F 2/72* (2013.01);
(Continued)

(58) Field of Classification Search
CPC ...... A61H 3/00; A61H 1/0255; A61H 1/0262; A61H 3/04; A61H 2003/006;
(Continued)

(56) References Cited

U.S. PATENT DOCUMENTS

| 6,645,126 B1 | 11/2003 | Martin et al. |
| 8,623,098 B2 | 1/2014 | Goldfarb et al. |

(Continued)

FOREIGN PATENT DOCUMENTS

| JP | 2012-95793 A | 5/2012 |
| KR | 10-1221046 B1 | 2/2013 |

(Continued)

OTHER PUBLICATIONS

Den Otter, A. R., et al. "Speed related changes in muscle activity from normal to very slow walking speeds." Gait & posture 19.3 (2004): 270-278.

(Continued)

*Primary Examiner* — Steven O Douglas
(74) *Attorney, Agent, or Firm* — NSIP Law

(57) ABSTRACT

A walk assist robot for lower body walking of a walking trainee, including a joint angle signal measurement unit disposed on a joint of the walking trainee, an electromyogram (EMG) signal measurement unit disposed on a muscle related to ankle joint extension of the walking trainee, a plantar pressure signal measurement unit disposed on a sole of the walking trainee, and a control unit to recognize signals measured from the joint angle signal measurement unit, the EMG signal measurement unit and the plantar pressure signal measurement unit and process the signals to recognize a walking speed intention of the walking trainee, wherein the control unit controls a walking speed of the walk assist robot from the walking speed intention of the walking trainee.

17 Claims, 10 Drawing Sheets

(51) Int. Cl.
  *A61F 2/72*      (2006.01)
  *A61B 5/0488*    (2006.01)
  *A61H 1/02*      (2006.01)
  *B25J 9/00*      (2006.01)
  *A61B 5/107*     (2006.01)
  *A63B 69/00*     (2006.01)
  *A63B 21/005*    (2006.01)
  *A63B 21/068*    (2006.01)
  *A63B 21/16*     (2006.01)
  *A63B 22/02*     (2006.01)
  *A63B 24/00*     (2006.01)
  *A63B 21/00*     (2006.01)
  *A61H 3/04*      (2006.01)

(52) U.S. Cl.
  CPC ......... *A61H 1/0255* (2013.01); *A61H 1/0262* (2013.01); *B25J 9/0006* (2013.01); *A61B 5/1071* (2013.01); *A61H 3/04* (2013.01); *A61H 2003/006* (2013.01); *A61H 2201/0119* (2013.01); *A61H 2201/1207* (2013.01); *A61H 2201/1463* (2013.01); *A61H 2201/164* (2013.01); *A61H 2201/1628* (2013.01); *A61H 2201/1635* (2013.01); *A61H 2201/1652* (2013.01); *A61H 2201/1664* (2013.01); *A61H 2201/1676* (2013.01); *A61H 2201/5007* (2013.01); *A61H 2201/5069* (2013.01); *A61H 2201/5071* (2013.01); *A61H 2230/605* (2013.01); *A63B 21/0058* (2013.01); *A63B 21/00181* (2013.01); *A63B 21/068* (2013.01); *A63B 21/16* (2013.01); *A63B 21/4011* (2015.10); *A63B 21/4013* (2015.10); *A63B 21/4015* (2015.10); *A63B 22/02* (2013.01); *A63B 69/0059* (2013.01); *A63B 2024/0093* (2013.01); *A63B 2069/0062* (2013.01); *A63B 2220/34* (2013.01); *A63B 2220/56* (2013.01); *A63B 2230/605* (2013.01)

(58) Field of Classification Search
  CPC .... A61H 2201/0119; A61H 2201/1207; A61H 2201/1463; A61H 2201/1628; A61H 2201/1635; A61H 2201/164; A61H 2201/1652; A61H 2201/1664; A61H 2201/1676; A61B 5/04888; A61B 5/1038; A61F 2/72
  See application file for complete search history.

(56) References Cited

U.S. PATENT DOCUMENTS

| | | | |
|---|---|---|---|
| 8,684,890 B2 | 4/2014 | Bosecker et al. | |
| 9,526,636 B2 * | 12/2016 | Bedard | A61F 2/66 |
| 2007/0162152 A1 * | 7/2007 | Herr | A61F 2/60 |
| | | | 623/24 |
| 2014/0058299 A1 | 2/2014 | Sankai et al. | |
| 2015/0134080 A1 | 5/2015 | Roh | |

FOREIGN PATENT DOCUMENTS

| | | |
|---|---|---|
| KR | 10-1323019 B1 | 10/2013 |
| KR | 10-2015-0055958 A | 5/2015 |
| WO | WO 2012/118143 A1 | 9/2012 |

OTHER PUBLICATIONS

Liu, May Q., et al. "Muscle contributions to support and progression over a range of walking speeds." Journal of biomechanics 41.15 (2008): 3243-3252.

* cited by examiner

Prior Art

RECOGNITION METHOD OF HUMAN WALKING SPEED INTENTION FROM SURFACE ELECTROMYOGRAM SIGNALS OF PLANTAR FLEXOR AND WALKING SPEED CONTROL METHOD OF A LOWER-LIMB EXOSKELETON ROBOT

CROSS-REFERENCE TO RELATED APPLICATION

This application claims priority to Korean Patent Application No. 10-2015-0123027, filed on Aug. 31, 2015, and all the benefits accruing therefrom under 35 U.S.C. § 119, the contents of which in its entirety are herein incorporated by reference.

BACKGROUND

1. Field

The present disclosure relates to a method which recognizes a walking speed intention of a walking trainee wearing a walk assist robot and controls a walking speed of the walk assist robot using the same.

Specifically, the present disclosure relates to a method which recognizes a walking speed intention of a walking trainee from surface electromyogram (EMG) of muscles related to ankle joint extension in the plantar flexor of the walking trainee, and a method which controls a walking speed of a walk assist robot using the same.

Also, the present disclosure relates to a method which selects a linear or non-linear function in proportion to a plantar flexor EMG waveform length maximum value in the stance phase during the gait cycle of a walking trainee, sets coefficients of the function, and recognizes a walking speed intention, and a method which observes changes in plantar pressure or knee joint angle of a walking trainee and determines the end of stance phase, and a method which controls a walking speed of a walk assist robot to conform to a walking speed intention of a walking trainee.

[Description about National Research and Development Support]

This study was supported by the Robot Industry Convergence Technology Development program of Ministry of Trade, Industry and Energy, Republic of Korea (Project No. 1415135300) under the Korea Evaluation Institute of Industrial Technology.

2. Description of the Related Art

Recently, walk assist robots such as exoskeleton type gait rehabilitation training robots and robots for increasing muscular strength are being actively developed. Also, many studies have been made on human-robot interfaces to intuitively operate these robots according to the intention of walking trainees. These studies are about making new intuitive human-robot interface protocols related to robot manoeuvre and applying them to robots, rather than a direct intention related to gait of walking trainees.

A conventional example of this walk assist robot is disclosed in FIG. 10.

The conventional walk assist robot 100 includes a chair 101 and a body weight support system 108 to support a body of a walking trainee, and the body weight support system 108 is supported on a supporting member 103.

Also, through a height adjustment device 102, the height of the body weight support system 108 can be adjusted based on a body size of the walking trainee, and a speed controller 107 disposed at the lower part of the walk assist robot 100 controls the speed of a conveyor 106, and controls the speed of a treadmill 104 through a hinge mechanism 105 connected to the conveyor 106.

However, the conventional walk assist robot 100 can control the walking speed, but simply controls the speed of the treadmill 104 only by a control method of the walk assist robot 100 itself, and does not consider a walking intention of the walking trainee at all.

Thus, there is a need for technology that finds a direct walking intention from bio-signals of walking trainees and applies it to robots, and particularly, in the case of gait rehabilitation training robots, such technology is essential.

Gait rehabilitation training robots are being clinically used mainly for hemiplegic patients after stroke, and their goal is to restore damaged brain functions related to gait through gait training. Thus, what is needed to increase a rehabilitation effect of gait rehabilitation training is not new intuitive human-robot interface protocols, but identifying instructions related to gait carried from the brain to lower limb muscles and controlling robots in accordance with the instructions.

Also, through this, there is a need for development of walk assist robots that contribute to the reduction in social costs for taking care of walking trainees by enabling them to walk almost like normal people independently without wearing robots when they finish rehabilitation training.

Related Literatures

U.S. Pat. No. 8,623,098

SUMMARY

To solve the problem, the present disclosure is intended to control a walking speed of a walk assist robot based on the recognition of a walking speed intention using noninvasive surface electromyogram (EMG) signals, rather than recognition of an exercise intention of each joint, in order to enable a walking trainee to walk.

Also, the present disclosure is intended to provide a walk assist robot for resolving a conflict between a walking speed intention of a walking trainee and a stable walking trajectory of a walk assist robot and a method of controlling a walking speed of a walk assist robot.

To achieve the objects, the present disclosure provides a walk assist robot for lower body walking of a walking trainee, including a joint angle signal measurement unit disposed on a joint of the walking trainee, an EMG signal measurement unit disposed on a muscle related to ankle joint extension of the walking trainee, a plantar pressure signal measurement unit disposed on a sole of the walking trainee, and a control unit to recognize signals measured from the joint angle signal measurement unit, the EMG signal measurement unit and the plantar pressure signal measurement unit and process the signals to recognize a walking speed intention of the walking trainee, wherein the control unit controls a walking speed of the walk assist robot from the walking speed intention of the walking trainee.

Also, the control unit of the present disclosure may further include a signal processing unit to process the joint angle signal and the plantar pressure signal, a waveform length calculation unit to calculate a waveform length from the EMG signal, and a stance phase determination unit to determine a stance phase range of walking of the walking trainee.

Also, in the present disclosure, the walking speed intention of the walking trainee may be repetitively recognized each point in time at which the stance phase of walking ends, and the EMG signal measurement unit may be arranged at a position of at least one of soleus, gastrocnemius, and peroneus longus muscles in the muscle related to ankle joint extension of the walking trainee.

Also, the plantar pressure signal measurement unit of the present disclosure may be arranged at a position of at least one of a medial forefoot, a lateral forefoot and a rearfoot of left and right soles of the walking trainee, and the joint angle signal measurement unit may be arranged at left and right knee joints or angle joints of the walking trainee.

Also, the control unit of the present disclosure may estimate a walking speed intention in a swing phase during a gait cycle of the walking trainee, using a maximum value of the waveform length of the EMG signal in the stance phase during the gait cycle of the walking trainee.

Also, the present disclosure provides a method of controlling a walking speed of a walk assist robot using the walk assist robot described above, the method including measuring a joint angle signal from the joint angle signal measurement unit, measuring an EMG signal from the EMG signal measurement unit, measuring a plantar pressure signal from the plantar pressure signal measurement unit, performing primary signal-processing of at least one of the joint angle signal, the EMG signal and the plantar pressure signal, calculating a waveform length from the primary signal-processed EMG signal, determining a stance phase from the primary signal-processed joint angle signal and the primary signal-processed plantar pressure signal, recognizing a walking speed intention from the waveform length and the stance phase, generating a walking trajectory of the walk assist robot from the walking speed intention, and controlling a walking speed of the walk assist robot from the walking trajectory of the walk assist robot.

Through the present disclosure, a walking speed intention of a walking trainee and a method of controlling a walking speed of a walk assist robot using the same may be applied to human-robot interfaces in gait rehabilitation training robots and robots for increasing muscular strength, and may be used for a robot to change its walking speed according to a robot wearer's intention.

DETAILED DESCRIPTION

Figure 1:
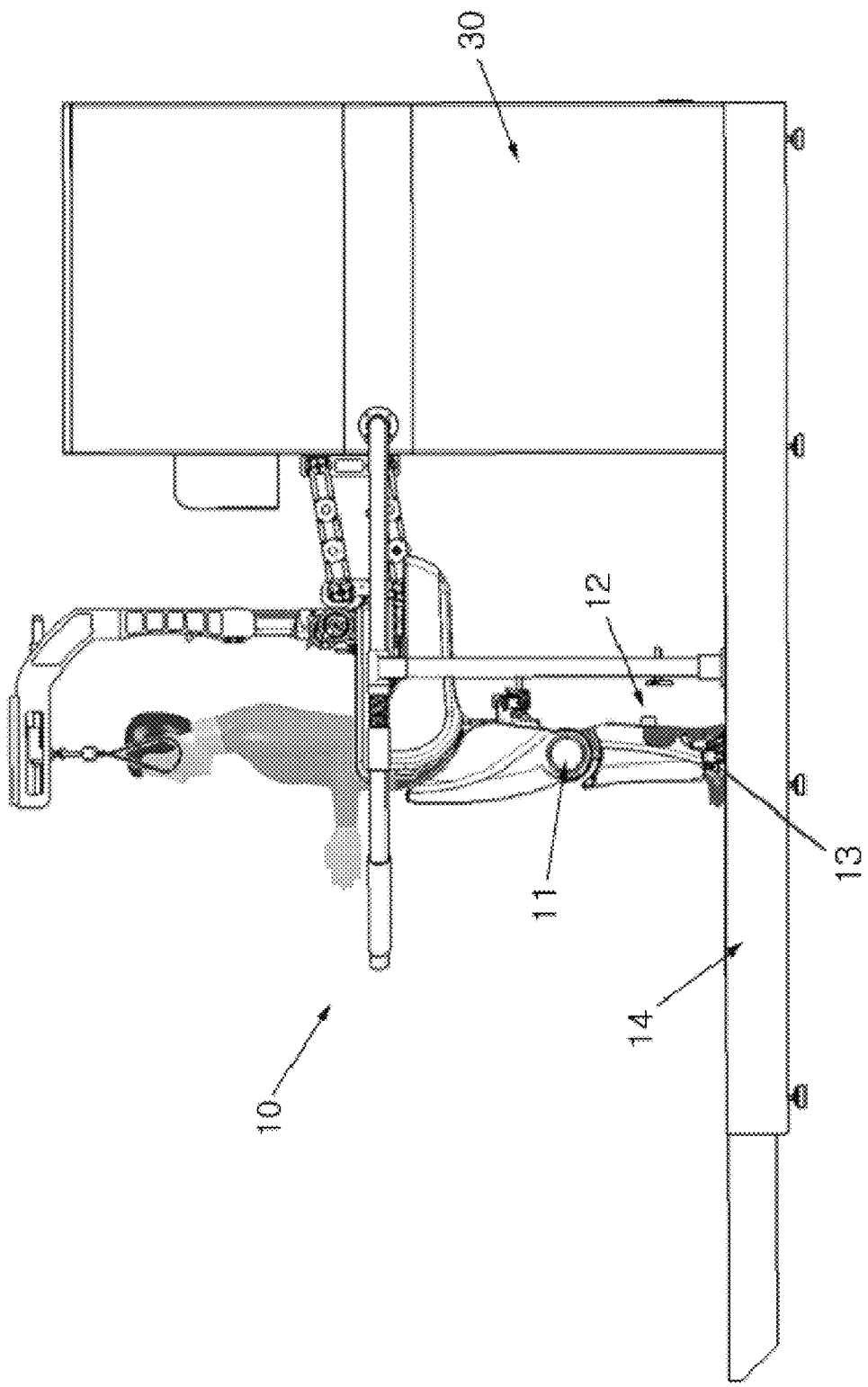
FIG. 1 is a schematic side view showing a walk assist robot according to an embodiment of the present disclosure.

Hereinafter, a walk assist robot and a method of controlling a walking speed of a walk assist robot according to the present disclosure is described through the preferred embodiments of the present disclosure with reference to the accompanying drawings.

Prior to the description, in many embodiments, one representative embodiment is described using the same reference numerals for elements having the same configuration, and the other embodiments are only described for the other elements.

FIG. 1 is a schematic side view showing a walk assist robot according to an embodiment of the present disclosure. As shown in FIG. 1, a walking trainee stands in a right position on the walk assist robot 10 according to an embodiment of the present disclosure.

Specifically, a treadmill 14 is arranged at the lower part of the walk assist robot 10, and the operating speed of the treadmill 14 may be changed through signals from a control unit 30.

Also, a joint angle signal measurement unit 11 is arranged at knee joints or ankle joints of the walking trainee, an electromyogram (EMG) signal measurement unit 12 is arranged at the position of muscles related to extension of the ankle joints of the walking trainee, and a plantar pressure signal measurement unit 13 is arranged at the position of soles of the walking trainee.

Signals measured from the joint angle signal measurement unit 11, the EMG signal measurement unit 12 and the plantar pressure signal measurement unit 13 are transmitted to the control unit 30, and a walking speed intention of the walking trainee is recognized through signal processing as described later.

Figure 2:
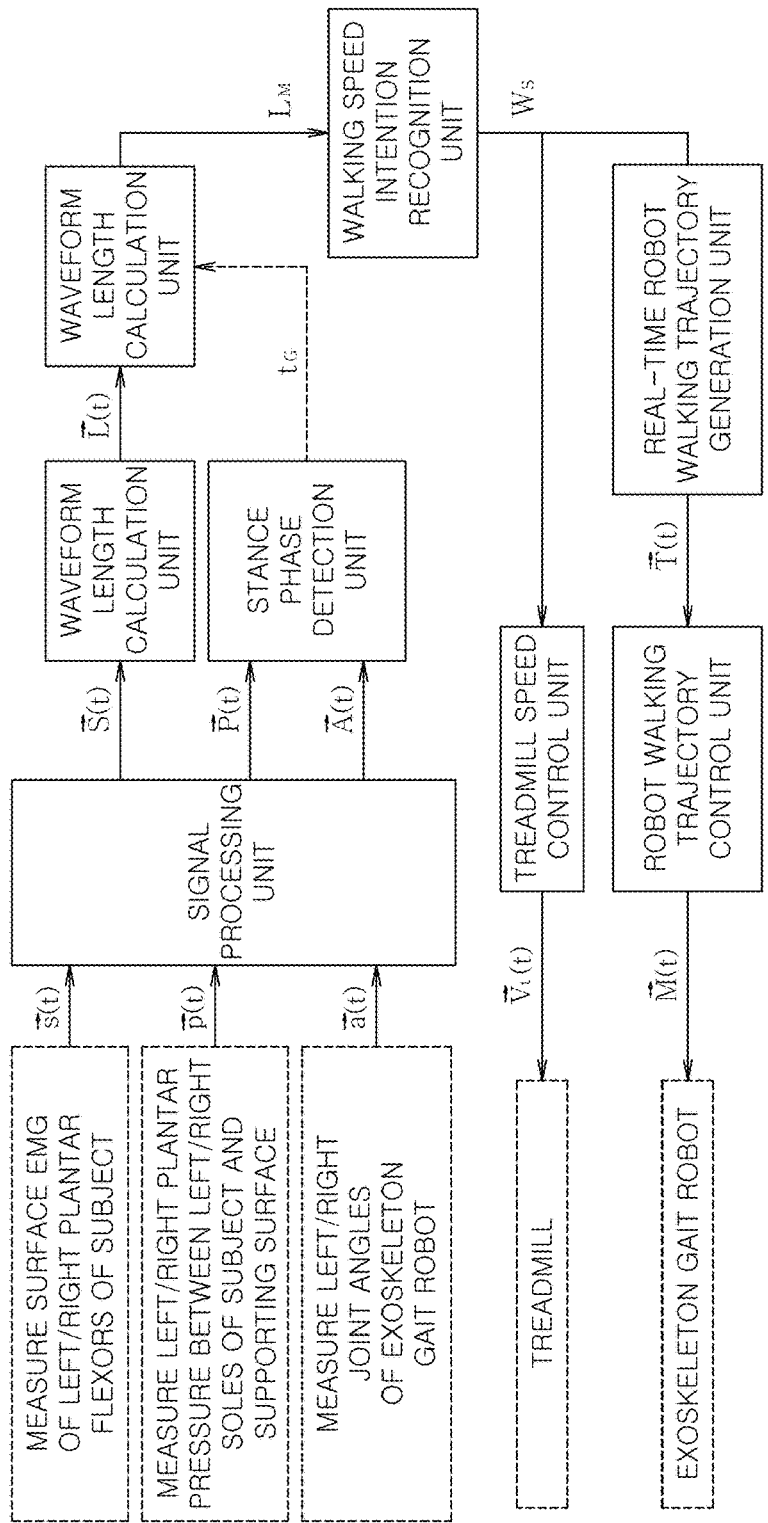
FIG. 2 is a schematic block diagram showing a method of controlling a walk assist robot according to an embodiment of the present disclosure.

FIG. 2 is a schematic block diagram showing a method of processing, by the control unit 30, the signals measured from the joint angle signal measurement unit 11, the EMG signal measurement unit 12 and the plantar pressure signal measurement unit 13 of the walk assist robot according to an embodiment of the present disclosure.

As shown in FIG. 2, joint angle signals $\vec{a}(t)$, plantar pressure signals $\vec{p}(t)$ and EMG signals $\vec{s}(t)$ from a subject getting on the walk assist robot are measured.

The EMG signals are measured from at least one of soleus, gastrocnemius, and peroneus longus muscles related to ankle joint extension in the left and right plantar flexors, for example, 2, 4 or 6 muscles of left and right legs.

The plantar pressure signals are measured by pressure sensors attached to 3-4 points on a medial forefoot, a lateral forefoot and a rearfoot of left and right soles, for example, 6 or 8 points on left and right soles.

The joint angle signals are measured by encoders attached to left and right knee joints or ankle joints of the robot, for example, 2 or 4 joints of left and right legs.

Here, either the joint angle signals or the plantar pressure signals or both of them may be measured.

The signals measured as described in the foregoing are passed through a signal processing unit (a band-pass filter or a low-pass filter) that performs signal processing based on the characteristics of each signal, and the signal-processed EMG signals $\vec{S}(t)$ are inputted to a waveform length calculation unit and used to calculate a waveform length $\vec{L}(t)$ by a method such as the following equation 1.

$$\vec{L}(t) = \sum_{n=t-N+2}^{t} |\vec{S}(n) - \vec{S}(n-1)| \quad (1)$$

On the other hand, the signal-processed plantar pressure signals $\vec{P}(t)$ and the signal-processed joint angle signals $\vec{A}(t)$ are inputted to a stance phase determiner of the control unit 30 to determine a stance phase range of the gait phase.

The stance phase determiner finds the beginning $t_1$ and the end $t_2$ of the stance phase of each leg using either the signal-processed plantar pressure signals or the signal-processed joint angle signals or both of them.

Then, a stance phase range maximum value detection unit finds a waveform length maximum value $L_M$ during the stance phase duration in a way such as the following equation 2, and a walking speed intention recognition unit recognizes a walking speed intention $W_S$ in a way such as equation 3. Here, the function $f(\cdot)$ is a function that defines a proportional relationship between the waveform length maximum value and the walking speed intention, and may be a linear function, a polynomial function, or a non-linear function.

$$L_M = \max_{t_1 \leq t \leq t_2} \vec{L}(t) \quad (2)$$

$$W_S = f(L_M) \quad (3)$$

The walking speed intention is recognized each point in time at which the stance phase ends during walking, and is inputted to a real-time robot walking trajectory generation unit and a speed control unit of the treadmill 14 to generate a walking trajectory $\vec{T}(t)$ of the robot in real time and control the speed of the treadmill 14 and the walking speed of the walk assist robot 10.

Figure 3:
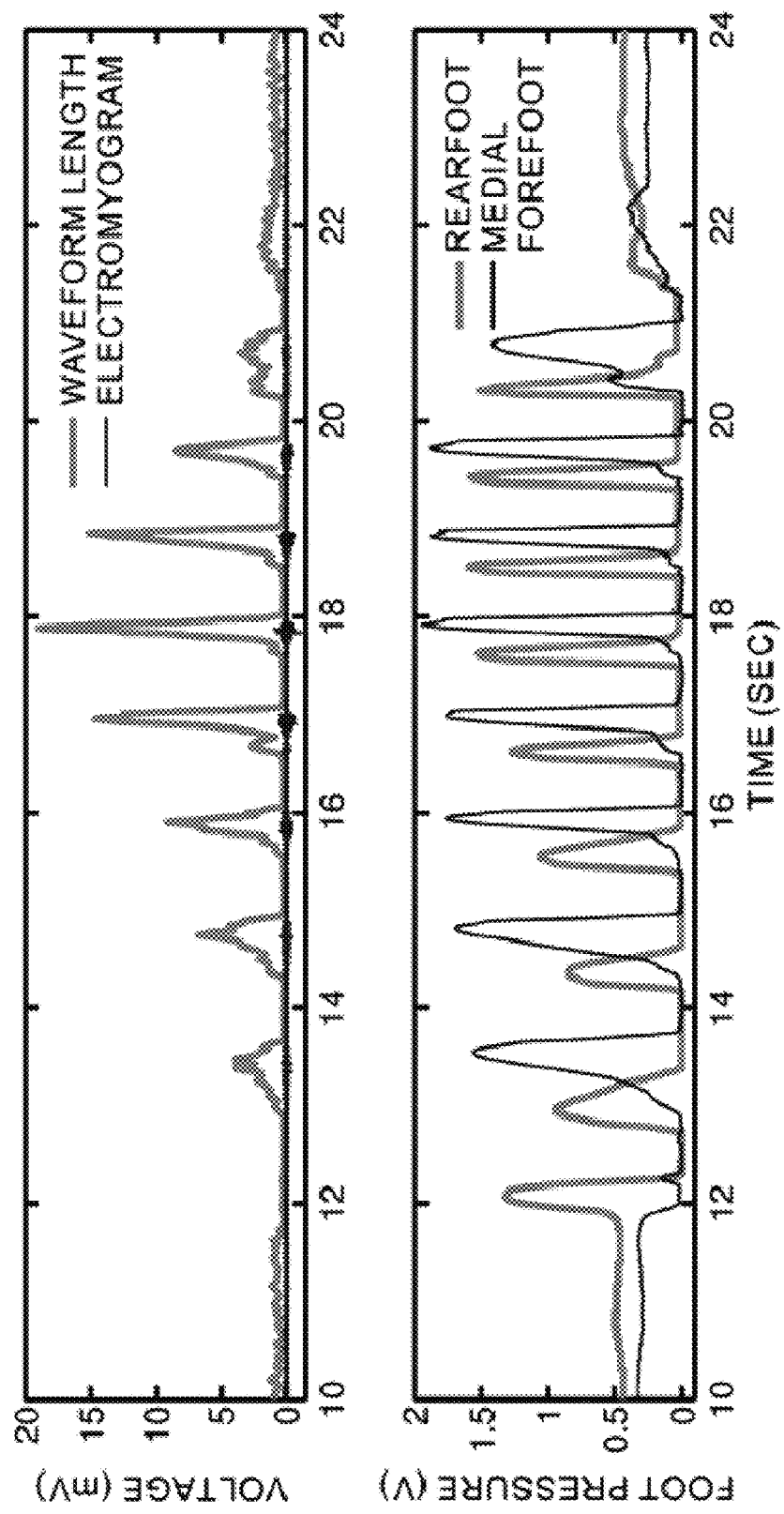
FIG. 3 is a graph showing surface electromyogram (EMG) and a waveform length of a walking trainee, and plantar pressure in an inside forefoot and a rearfoot of a right foot of the walking trainee while walking.

FIG. 3 is a graph showing surface EMG and a waveform length, and plantar pressure in a medial forefoot and a rearfoot of a right foot of a walking trainee while walking.

In FIG. 3, the unit of X axis is second (sec), and the unit of Y axis is voltage (volt). It can be seen that a soleus surface EMG waveform length maximum value in the stance phase increases with the increasing walking speed.

Figure 4:
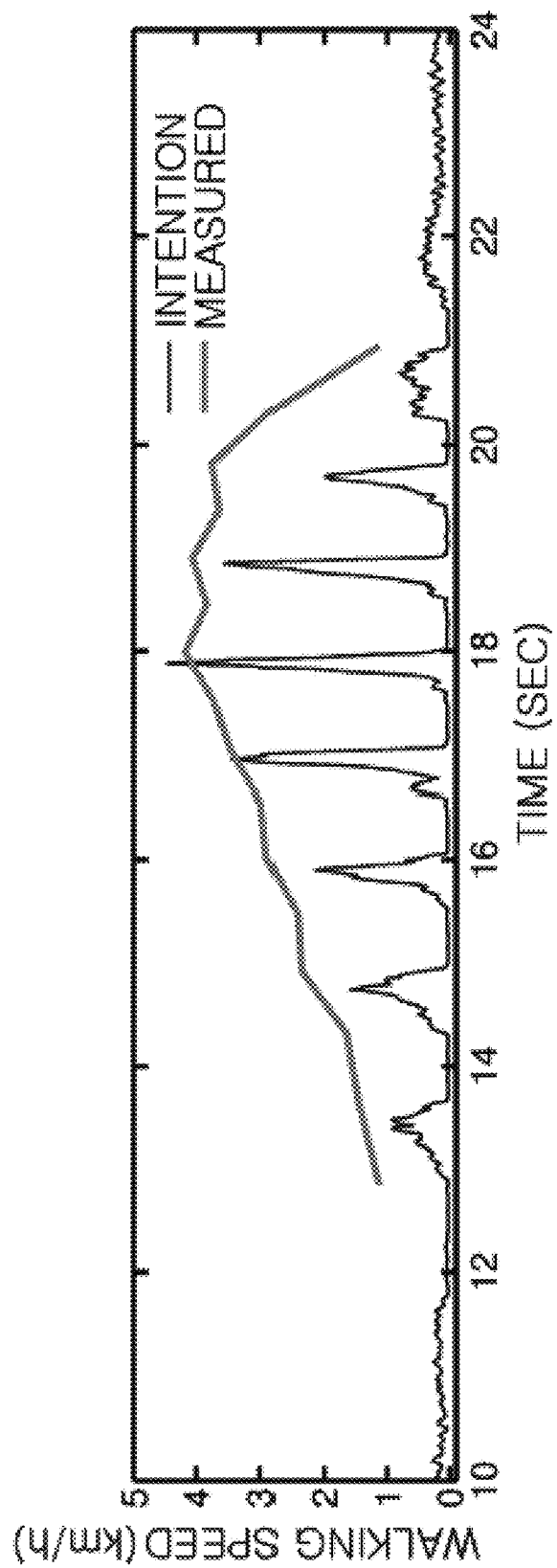
FIG. 4 is a graph for a comparison of an actual walking speed of a walking trainee and a walking speed intention according to an embodiment of the present disclosure.

To compare to a walking speed, the function $f(\cdot)$ in equation 3 is simply defined as a first degree directly proportional function as shown in the following equation 4 to recognize a walking speed, and a comparison to an actual walking speed is as shown in FIG. 4.

$$W_S = K \times L_M \quad (4)$$

Accordingly, a speed intention of the walking trainee may be recognized by suitably selecting a gain K, an assisting force of the walk assist robot may be increased or decreased by adjusting the dimension of gain, and a more accurate walking speed intention may be recognized by non-linearly selecting the gain K as a function of $L_M$ and changing it based on the waveform length maximum value.

Figure 5:
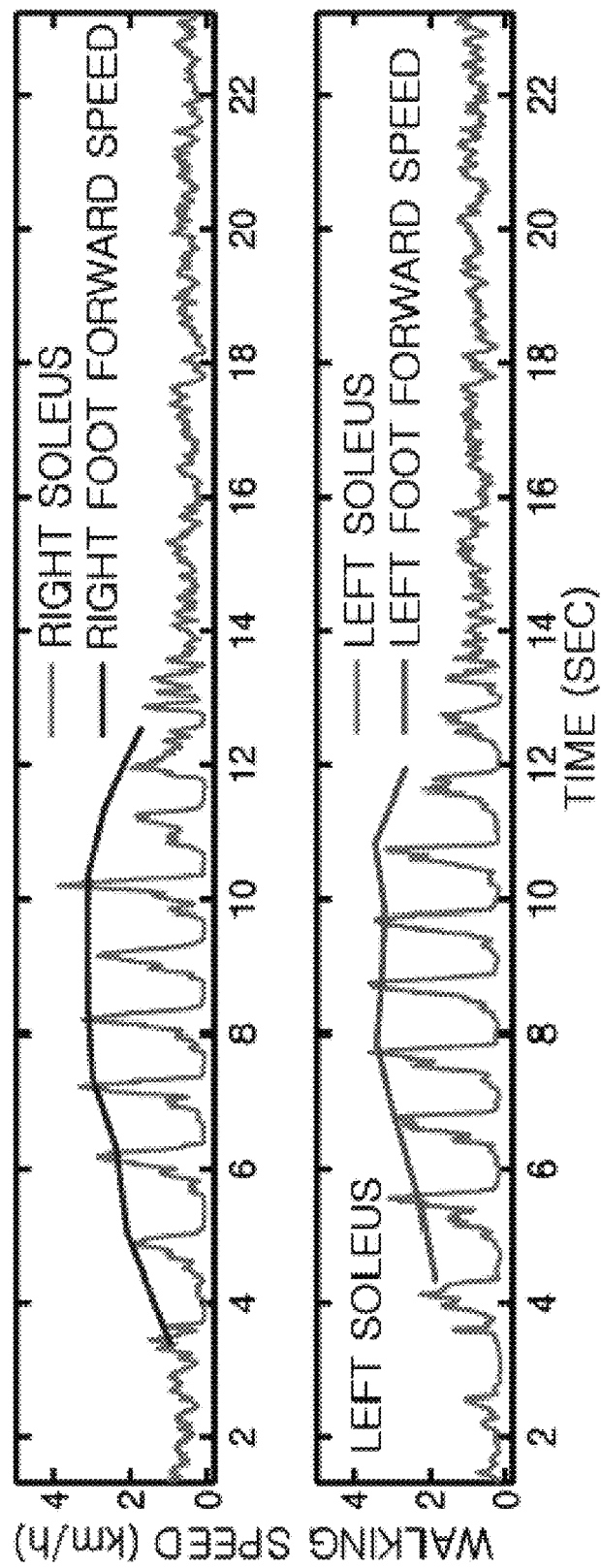
FIG. 5 is another graph for a comparison of an actual walking speed of a walking trainee and a walking speed intention according to an embodiment of the present disclosure.

For example, referring to FIG. 5, it can be also seen from an actual walking speed during flatland accelerated walking of a hemiplegic patient after stroke (a 63-year-old male patient with chronic hemiparesis for 15 years after paralysis on the left side), and a result of multiplying an EMG waveform length of soleus by the gain K in equation 4 that a walking speed intention may be recognized from EMG of unaffected side as well as EMG of affected side as shown in FIG. 5. Thus, it can be seen that the control method of the present disclosure can be thoroughly applied to hemiplegic patients after stroke to recognize a walking speed intention.

Figure 6:
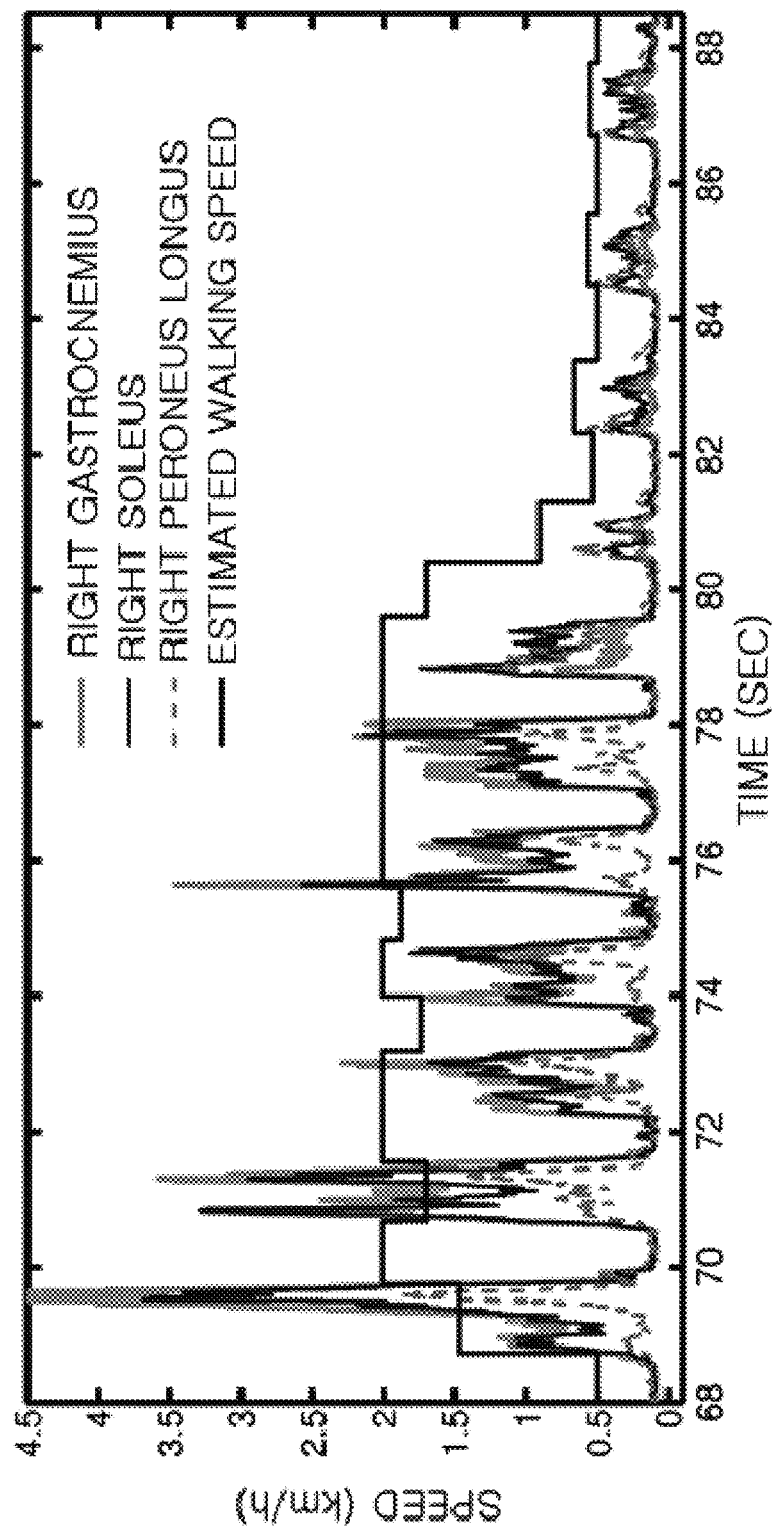
FIG. 6 is a graph for a comparison of EMG signals and a walking speed intention of a walking trainee and a walking speed of a walk assist robot according to one embodiment of the present disclosure.

FIG. 6 is a graph showing a result of applying to an exoskeleton type gait rehabilitation robot based on the treadmill 14 to demonstrate one embodiment of the present disclosure.

A non-disabled man in his early 30s got on a walk assist robot as shown in FIG. 6 and walked according to his intention. FIG. 6 shows a result of multiplying EMG waveform lengths of soleus, gastrocnemius, and peroneus longus of a right leg by the gain K in equation 4, and a walking speed intention recognized from equation 4.

In FIG. 6, the reason why the walking speed intention does not exceed 2 Km/h is that the walking speed of the walk assist robot is programmatically limited to 2 Km/h for safety of the subject. It can be seen from FIG. 6 that the walk assist robot is walking according to an intention of the subject by using one embodiment of the present disclosure. Thus, it can be seen that the walk assist robot recognizes a walking speed intention from only EMG signals by the control method according to one embodiment of the present disclosure and is walking according to the result.

Also, when a waveform length of surface EMG of muscles related to extension of ankle joints in plantar flexor while he is standing still is higher than or equal to a particular value, it is recognized as an intention to start walking with the other foot's forward step, and when a waveform length maximum value in the stance phase while he is walking is lower than or equal to a particular value, it is recognized as an intention to stop walking. Thus, the walking trainee's intention to start walking and stop walking can be recognized.

Figure 7:
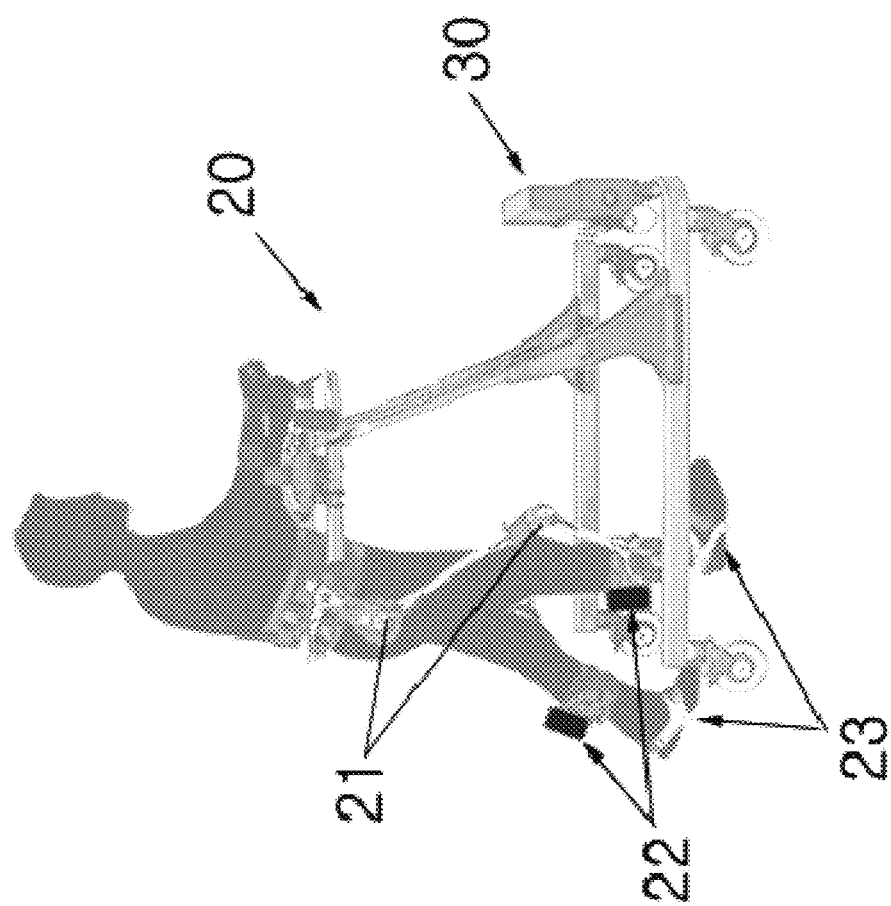
FIG. 7 is a schematic perspective view showing a walk assist robot according to another embodiment of the present disclosure.

FIG. 7 is a schematic perspective view showing a walk assist robot according to another embodiment of the present disclosure, and it is applied to an exoskeleton walk assist robot 20 with no treadmill 14 for ground gait rehabilitation training dissimilar to the previous embodiment.

Figure 8:
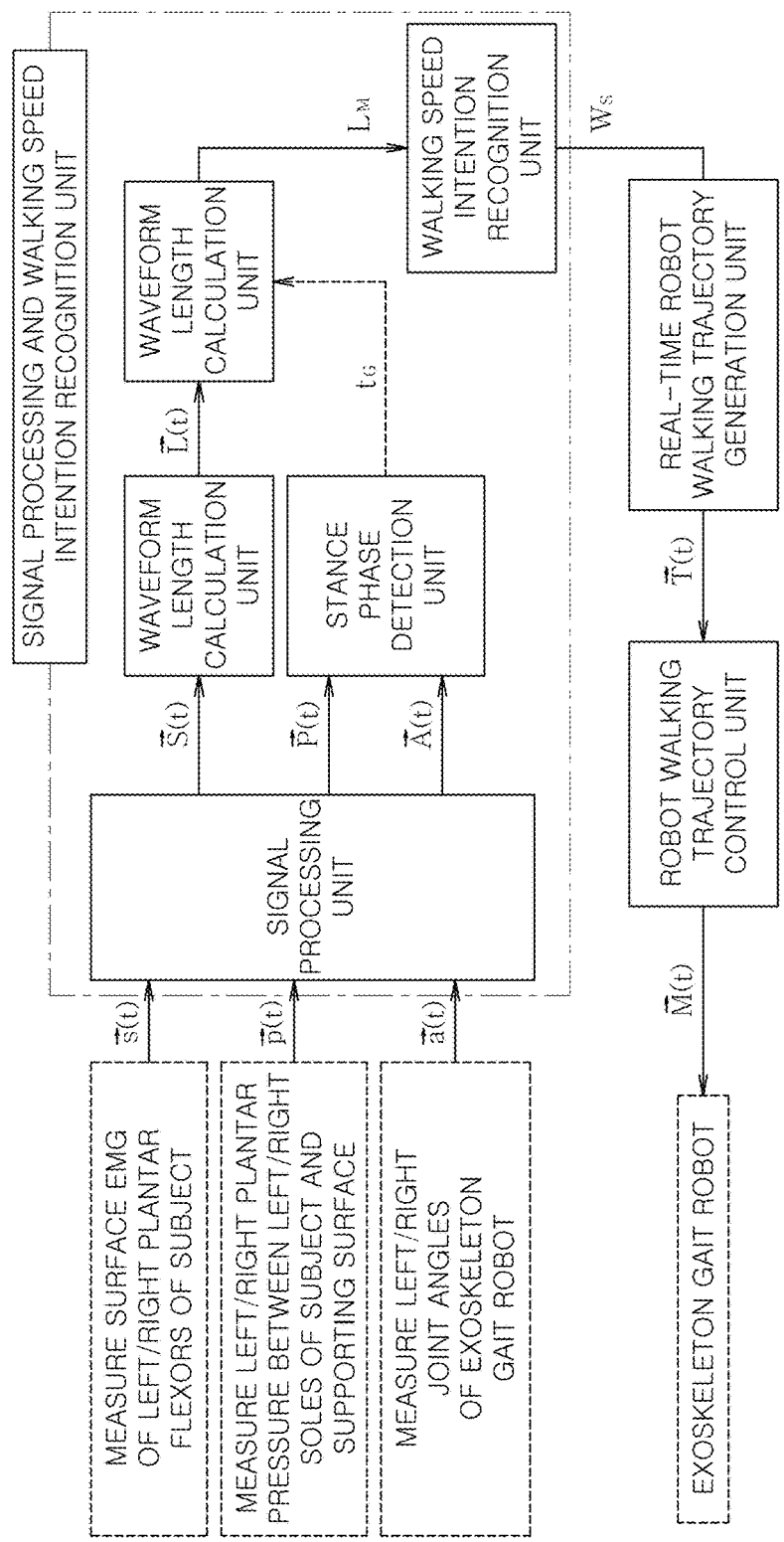
FIG. 8 is a schematic block diagram showing a method of controlling a walk assist robot according to another embodiment of the present disclosure.
Figure 9:
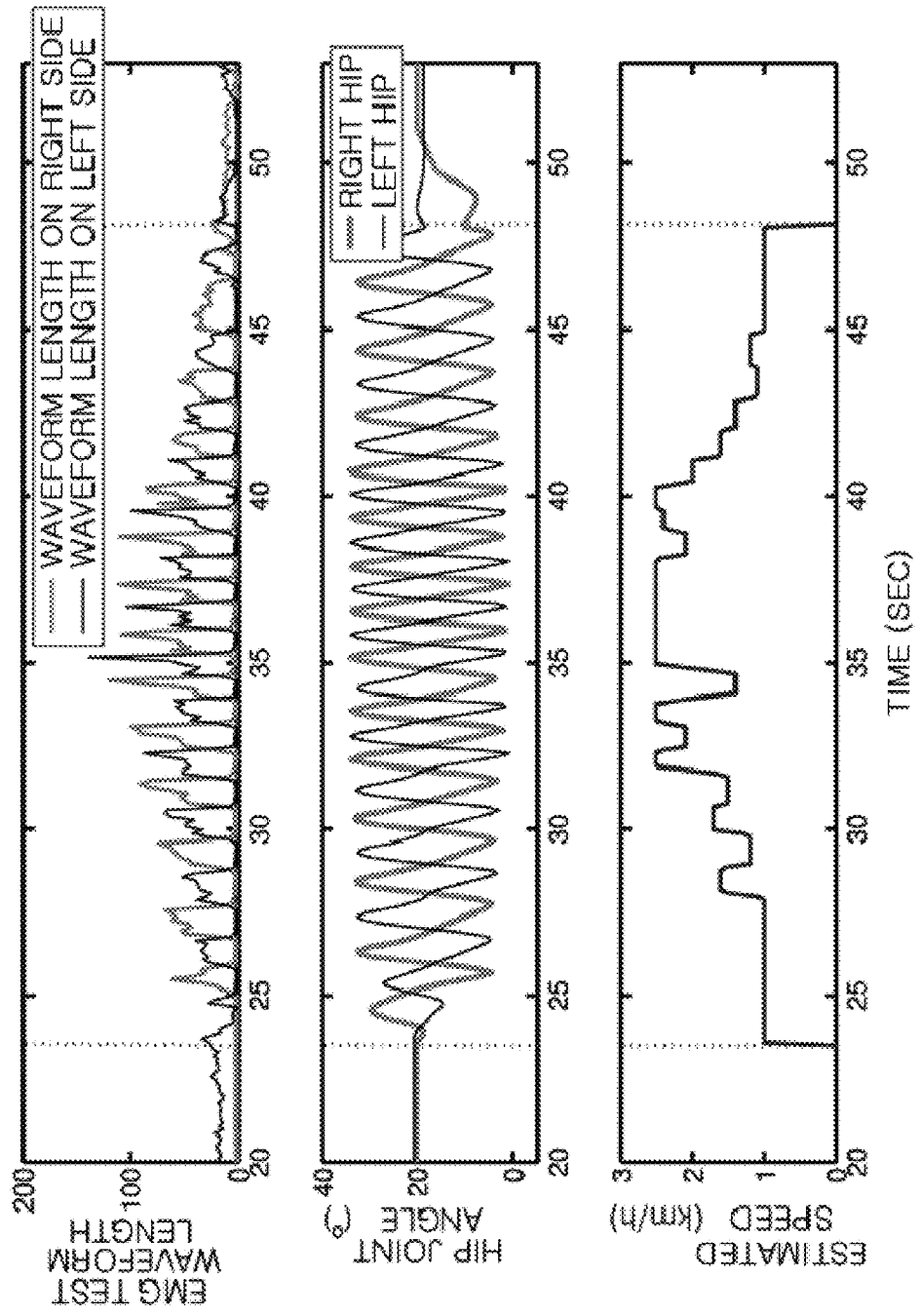
FIG. 9 is a graph for a comparison of EMG signals, joint angle signals and a walking speed intention of a walking trainee according to another embodiment of the present disclosure.
Figure 10:
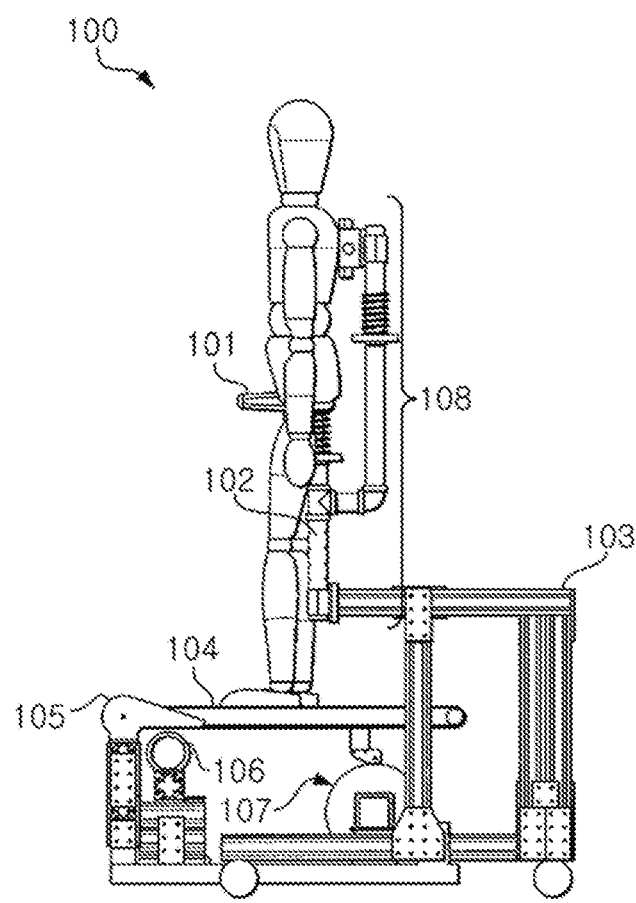
FIG. 10 is a schematic side view of a walk assist robot according to related art.

This another embodiment of the present disclosure is controlled as shown in FIG. 8, and EMG signals, joint angle signals and a walking speed intention of a walking trainee are shown in FIG. 9.

The specific operation method or control method of this another embodiment of the present disclosure is the same as the previous embodiment except that the tread mill 14 is omitted, and its detailed description is omitted herein.

As such, those skilled in the art will understand that the present disclosure may be embodied in other specific forms without any change to its technical aspect or essential feature.

Therefore, it should be understood that the embodiments described hereinabove are for illustration in all aspects and are not intended to limit the above embodiments, and it should be construed that the scope of the present disclosure is defined by the appended claims rather than the above detailed description, and the meaning and scope of the claims and all changes or modifications derived from equivalent concepts fall within the scope of the present disclosure.

The present disclosure is applied to gait rehabilitation robots and medical equipment for lower limb rehabilitation capable of reflecting an intention to implement EMG based walking speed intention detection technique, thereby providing rehabilitation therapy with an addition of a top-down rehabilitation approach to an existing bottom-up rehabilitation approach, which is applied to stroke patients to implement rehabilitation therapy capable of adjusting a walking speed according to patients' intention.

Also, the present disclosure is applied to walk assist robots to implement EMG based walking speed detection technique, and through this, the present disclosure may recognize a walking speed intention of a user and allow a walk assist robot to make movements and assist walking according to the user's intention.

| Reference Symbols | |
|---|---|
| 10: Walk assist robot | 11: Joint angle measurement unit |
| 12: EMG measurement unit | 13: Plantar pressure measurement unit |
| 14: Treadmill | 30: Control unit |
| 20: Exoskeleton walk assist robot | |
| 21: Joint angle measurement unit | 22: EMG measurement unit |
| 23: Plantar pressure measurement unit | 30: Control unit |

What is claimed is:

1. A walk assist robot for lower body walking of a walking trainee, comprising:
   a joint angle sensor adapted to be disposed on a joint of the walking trainee;
   an electromyogram (EMG) signal sensor adapted to be disposed on a muscle related to ankle joint extension of the walking trainee;
   a plantar pressure sensor adapted to be disposed on a sole of the walking trainee; and
   a controller configured to recognize measured signals from the joint angle sensor, the EMG signal sensor, and the plantar pressure sensor, and process the recognized signals to recognize a walking speed intention of the walking trainee,
   wherein the controller controls a walking speed of the walk assist robot from the recognized walking speed intention of the walking trainee.

2. The walk assist robot according to claim 1, wherein the controller further comprises:
   a band-pass filter to process a joint angle signal from the joint angle sensor and plantar pressure signal from the plantar pressure sensor;
   a waveform length calculator to calculate a waveform length from an EMG signal from the EMG signal sensor; and
   a stance phase detector to detect a stance phase range of walking of the walking trainee.

3. The walk assist robot according to claim 2, wherein the walking speed intention of the walking trainee is repetitively recognized each point in time at which the stance phase of walking ends.

4. The walk assist robot according to claim 1, wherein the EMG signal sensor is adapted to be arranged at a position of at least one of soleus, gastrocnemius, and peroneus longus muscles in the muscle related to ankle joint extension of the walking trainee.

5. The walk assist robot according to claim 1, wherein the plantar pressure unit sensor is adapted to be arranged at a position of at least one of a medial forefoot, a lateral forefoot and a rearfoot of left and right soles of the walking trainee.

6. The walk assist robot according to claim 1, wherein the joint angle sensor is adapted to be arranged at left and right knee joints or angle joints of the walking trainee.

7. The walk assist robot according to claim 2, wherein the controller configured to estimate a walking speed intention in a swing phase during a gait cycle of the walking trainee, using a maximum value of the waveform length of the EMG signal in the stance phase during the gait cycle of the walking trainee.

8. A processor implemented method of controlling a walking speed of a walk assist robot using the walk assist robot, the method comprising:
   measuring a joint angle signal from a joint angle sensor;
   measuring an electromyogram (EMG) signal from an EMG signal sensor;
   measuring a plantar pressure signal from a plantar pressure sensor;
   performing the respective signal-processing of at least one of the joint angle signal from the joint angle sensor, the EMG signal from the EMG signal sensor, and the plantar pressure signal from plantar pressure sensor;
   calculating a waveform length from the signal-processed EMG signal;
   detecting a stance phase from the signal-processed joint angle signal and the signal-processed plantar pressure signal;
   recognizing a walking speed intention from the waveform length and the stance phase;
   generating a walking trajectory of the walk assist robot from the walking speed intention; and
   controlling a walking speed of the walk assist robot from the walking trajectory of the walk assist robot.

9. The method according to claim 8, wherein the joint angle sensor adapted to be disposed on a joint of the walking trainee;
   the electromyogram (EMG) signal sensor adapted to be disposed on a muscle related to ankle joint extension of the walking trainee; and
   the plantar pressure sensor adapted to be disposed on a sole of the walking trainee.

10. A walk assist robot system for lower body walking of a walking trainee, comprising:
    a joint angle sensor adapted, in the walk assist robot system, to be disposed on a joint of the walking trainee;
    an electromyogram (EMG) signal sensor adapted, in the walk assist robot system, to be disposed on a muscle related to ankle joint extension of the walking trainee;
    a plantar pressure sensor adapted, in the walk assist robot system, to be disposed on a sole of the walking trainee; and
    a controller configured to recognize measured signals from the joint angle sensor, the EMG signal sensor, and the plantar pressure sensor, and process the recognized signals to recognize a walking speed intention of the walking trainee,
    wherein the controller controls a walking speed of the walk assist robot from the walking speed intention of the walking trainee.

11. The system according to claim 10, further comprising the walk assist robot.

12. The system according to claim 10, wherein controller further comprises:

a band-pass filter to process a joint angle signal from the joint angle sensor and a plantar pressure signal from the plantar pressure sensor;

a waveform length calculator to calculate a waveform length from an EMG signal from the EMG signal sensor; and a stance phase detector to detect a stance phase range of walking of the walking trainee.

13. The system according to claim 10, wherein the walking speed intention of the walking trainee is repetitively recognized each point in time at which the stance phase of walking ends.

14. The system according to claim 10, wherein the EMG signal sensor is adapted, in the walk assist robot system, to be arranged at a position of at least one of soleus, gastrocnemius, and peroneus longus muscles in the muscle related to ankle joint extension of the walking trainee.

15. The system according to claim 10, wherein the plantar pressure sensor is adapted, in the walk assist robot system, to be arranged at a position of at least one of a medial forefoot, a lateral forefoot and a rearfoot of left and right soles of the walking trainee.

16. The system according to claim 10, wherein the joint angle sensor is adapted, in the walk assist system, to be arranged at left and right knee joints or angle joints of the walking trainee.

17. The walk assist robot according to claim 12, wherein the controller configured to estimate a walking speed intention in a swing phase during a gait cycle of the walking trainee, using a maximum value of the waveform length of the EMG signal in the stance phase during the gait cycle of the walking trainee.

* * * * *